United States Patent [19]

Arnold, Jr. et al.

[11] Patent Number: 5,185,439
[45] Date of Patent: Feb. 9, 1993

[54] ACRIDINIUM ESTER LABELLING AND PURIFICATION OF NUCLEOTIDE PROBES

[75] Inventors: Lyle J. Arnold, Jr.; Norman C. Nelson, both of San Diego, Calif.

[73] Assignee: Gen-Probe Incorporated, San Diego, Calif.

[21] Appl. No.: 332,939

[22] Filed: Dec. 12, 1988

Related U.S. Application Data

[63] Continuation-in-part of Ser. No. 105,080, Oct. 5, 1987, abandoned.

[51] Int. Cl.$^5$ .................. C07H 17/00; C12Q 1/68
[52] U.S. Cl. ........................ 536/24.3; 435/6
[58] Field of Search ................ 435/6; 536/27

[56] References Cited

U.S. PATENT DOCUMENTS

| | | | |
|---|---|---|---|
| 4,136,182 | 1/1979 | Crivello . | |
| 4,737,454 | 4/1988 | Dattagupta et al. | 435/6 |
| 4,739,044 | 4/1988 | Stabinsky | 536/27 |
| 4,935,263 | 5/1989 | Nguyen et al. | 536/27 |
| 5,030,557 | 7/1991 | Hogan | 435/6 |

FOREIGN PATENT DOCUMENTS

| | | |
|---|---|---|
| 0210449 | 2/1987 | European Pat. Off. . |
| 0212951 | 3/1987 | European Pat. Off. . |
| 0231495 | 8/1987 | European Pat. Off. . |
| 0233053 | 8/1987 | European Pat. Off. . |
| 2112779 | 12/1981 | United Kingdom . |

OTHER PUBLICATIONS

Septak, the Chemical Abstracts, 107:39648V (1987).
Hart et al., the Chemical Abstracts 107:232557t (1987).
Fieser Experiments in Organic Chemistry (1957) pp. 281–294 H. Heath & Co., U.S.
Weeks et al "Acridinium Esters as High-Specific-Activity Labels in Immunassay" *Clin. Chem.* vol. 29, #8, 1983, pp. 1474–1479.

*Primary Examiner*—John W. Rollins
*Attorney, Agent, or Firm*—Lyon & Lyon

[57] ABSTRACT

Methods for the construction, labelling and subsequent purification of nucleic acid probes containing primary amines with acridinium esters 4-(2-succinimidyloxycarbonyl-ethyl)phenyl-10-methylacridinium-9-carboxylate fluorosulfonate). The method for attaching acridinium esters to probes uses high (0.1 to 50 mM) acridinium ester concentrations achieved using organic solvent in concentrations of 20% to 80% by volume, and may be carried out either in solution, or with one or the other of the acridinium ester or the probe suspended in solution. Purification (the separation of labelled probe from unlabelled probe and free label) involves (1) first removing most of the free acridinium ester label from probe using rapid separation techniques, then (2) removing substantially all remaining free label from the probe and separating labelled probe from unlabelled probe, involves specific applications of ion exchange, reverse phase or hydroxyapatite HPLC.

17 Claims, 6 Drawing Sheets

FIG. 3.

LABELING OF PROBE WITH ACRIDINIUM ESTER

| CONJUGATION PARTNERS | REACTION PRODUCT | LABELLING CONDITIONS pH |
|---|---|---|
| −NH₂ + (N-hydroxysuccinimide ester) | −HN−C(=O)− | 7-9 |
| −NH₂ + CH₃O−C(=NH₂⁺)− (imidate) | −NH−C(=NH₂⁺)− | 8-10 |
| −NH₂ + (phthalimide ester) | −NH−C(=O)− | 7-9 |
| −NH₂ + SCN− | −NH−C(=S)−NH− | 7-9 |
| −NH₂ + O₂N−C₆H₄−O−C(=O)− (p-nitrophenyl ester) | −NH−C(=O)− | 7-9 |
| −NH₂ + H−C(=O)− (aldehyde) | −N=CH− | 7-9 |
| −SH + (maleimide) | −S− (succinimide adduct) | 6-9 |
| −SH + BrCH₂−C(=O)− | −S−CH₂−C(=O)− | 6-8 |
| −SH + RS−S−(2-pyridyl) | −S−S−R | 6-9 |
| −SH + Hg⁺−C₆H₄− | −S−Hg−C₆H₄− | 5-9 |

ACRIDINIUM ESTER LABELLING AND PURIFICATION OF NUCLEOTIDE PROBES

This is a continuation-in-part of application Ser. No. 105,080 filed Oct. 5, 1987, now abandoned.

FIELD OF THE INVENTION

The invention relates to methods and compositions for attaching detectable labels to diagnostic reagents. More specifically, it pertains to the labelling and purification of nucleotide probes with chemiluminescent acridinium esters for use in diagnostic hybridization assays.

BACKGROUND OF THE INVENTION

Prior Art

In the last twenty years, a wide variety of agents have been used as labels in clinical diagnostic and research assays. More recently, hybridization assays have been developed for sensitively detecting the presence of unique polynucleotide sequences. Typically, in such assays, a nucleotide multimer (probe) is labelled with an atom or group which can be readily detected.

When the labelled probe is exposed to a test sample suspected of containing a target nucleotide sequence, under hybridizing conditions, the target will hybridize with any such labelled probe. The presence of the target sequence in the sample can be determined qualitatively, or quantatively usually by separating hybridized and non-hybridized probe, then determining the amount of labelled probe which hybridized, either by determining the presence of label in probe hybrids, or by determining the quantity of label in non-hybridized probes.

Historically, radioactive labels were used. However, due to health hazards and difficulties in handling, non-isotopic labels were later developed. Such labels include those whose presence is determined either directly or indirectly. Examples of direct labels include chemiluminescent, fluorescent, or spectroscopically detectable labels. Examples of indirect labels include compounds, such as biotin and various antigens, which can be detected by means of proteins conjugated to an appropriate detectable label.

One preferred method for introducing labels into nucleotide multimer probes has been to introduce linker-arms into enzymatically or chemically synthesized probes. For example, 4-thio-UTP (H. Eshaghpour et al., Nucl. Acids Res., Vol. 7, p. 1485, 1979) has been attached to the 3'-end of DNA fragments and subsequently labelled at its nucleophilic sulfhydryl moiety. Another method disclosed in a PCT application by Tchen (International Publication No. WO 86/00074; published Jan. 3, 1986) disclosed a technique in which pyrimidine base nucleotides are depyrimidated, and the resulting sugar rings opened so that an amine bearing moiety can be attached thereto.

In addition, the 5-allylamine uridine triphosphate precursor analogs disclosed by P. R. Langer et al. (Proc. of Nat. Acad. Sci., U.S.A., Vol. 78, p. 6633, 1981), may be used for incorporating nucleophilic amines moieties into nucleotide multimer probes which provide sites for labelling.

Chemical methods for labelling have also been proposed which allow labels to be linked to nucleotides in a nucleotide multimer. One such method involves bisulfite catalyzed transamination with ethylenediamine at the C-4 position of cytosine residues of nucleic acid probes (R. P. Viscidi et al., J. Clin. Biol., Vol. 23, p. 311, 1986). Other techniques have been disclosed which allow attachment of only a single label at the 5'- or 3'-end of a nucleotide multimer, typically an oligonucleotide. For example, terminal labelling approaches have been disclosed which allow linker-arm attachment as a final step in solid-phase oligonucleotide synthesis. Such linker-arms are then employed for label attachment. For example, see B. A. Connolly, Nucl. Acids Res., Vol. 13, p. 4485, 1985; S. Agrawal et al., Nucl. Acids Res., Vol. 15, p. 3131, 1987.

Compounds have also been disclosed which can be used to insert a primary amine-modified nucleotide residue at selected positions in a synthetic oligonucleotide during standard automated synthesis procedures. Such compounds include analogs of deoxythymidine and deoxyadenine, deoxyguanine, etc. (G. B. Dreyer et al., Proc. Natl. Acad. Sci., U.S.A., Vol. 82, p. 968, 1985; J. L. Ruth, PCT application No. US84/00279, Publication No. WO 84/03285, published Aug. 30, 1984). In addition, alkylamine derivatives of nucleotide linking phosphate groups have been disclosed, the amino functional group of which can then be labelled (R. L. Letsinger and M. E. Schott, Jour. Amer. Chem. Soc., Vol. 103, p. 7394, 1981; Japanese patents to N. Sugimoto Nos. 61 44,353 issued Mar. 4, 1986; 61 57,595 issued Mar. 24, 1986; 61 44,352 issued Mar. 4, 1986). Theoretically, such compounds might allow for labelled nucleotides to be placed at a number of sites along a sequence, thus permitting use of multiple labels to increase sensitivity of detection. However, one must be careful in selecting linker-arm locations since some linker-arm sites can reduce the stability of a hybrid formed with a target sequence, particularly when multiple labels are present.

In addition to the linker-arms described above, we have designed non-nucleotide based linker-arm reagents which are disclosed in two pending patent applications to Arnold et al. entitled "Non-Nucleotide Linking Reagents for Nucleotide Probes" U.S. application Ser. No. 099,050 filed Sep. 21, 1987, now abandoned and "Non-Nucleotide Reagents for substituting the Termini of Oligonucleotides" U.S. application Ser. No. 104,330 filed Oct. 2, 1987, now abandoned. These linker-arm reagents overcome limitations of other prior-art reagents and allow attachment of linker-arms at a wide variety of sites as well as allowing the construction of nucleotide/non-nucleotide polymers.

One of the most sensitive classes of non-isotopic labels known are the chemiluminescent acridinium esters which have been described by Campbell et al., in U.K. patent No. 2112779B issued Oct. 15, 1986 and in Richardson et al., Chemiluminescence Immunoassay of Plasma Progesterone, with Progesterone-Acridinium Ester Used As the Labeled Antigen, Clin. Chem., Vol. 31, pp. 1664–1668 (1985), for attaching acridinium esters to proteins and hormones for use in immunodiagnostic assays. The attachment of acridinium esters to nucleotide probe multimers is not readily achieved using the labelling and purification procedures described for proteins. Labeling of nucleotide multimer probes with acridinium esters have been suggested earlier. However, such suggestions provide no method for labelling and purification (Yabusaki et al., U.S. Pat. No. 4,599,303) or the procedures described give poor extents of labelling and inadequate degrees of purification of labelled probes for use in hybridization assays (Mock et al., EPA Application No. 86306305.3 filed Aug. 15, 1986, Publication No. 0212951). The method described by Mock and Septek, for example, describes a procedure analogous to that for labelling and purifying proteins (Weeks et al.). We have found that such methods are inadequate for labelling oligonucleotide probes containing amineterminated linker-arms to any significant extent (≦10%). Moreover, the gel filtration methods employed for purifying acridinium ester labelled proteins do not separate labelled and unlabelled probe nor do they adequately remove unconjugated label. For use in hybridization diagnostic assays, it is necessary that neither significant amounts of unlabelled probe be present, since such unlabelled probes will compete in hybridization reactions with labelled probes, nor that the purified sample consists of more than 1% unconjugated label since unconjugated label binds to separation supports and creates high chemiluminescent background which greatly reduces the sensitivity of diagnostic assays. What is needed are means for labelling nucleotide multimers and purifying labelled multimers in essentially a pure form. The invention described herein provides such means.

OBJECTS OF THE INVENTION

It is an object of the present invention to label probes with acridinium ester and to purify probes so labelled to a high degree of purity. Prior art systems for (1) labbelling nucleotide probes with acridinium esters and purifying said labelled probes; and (2) labelling proteins with acridinium esters and purifying said labelled proteins proved unsatisfactory to this objective. Particularly, the prior art teaches the labelling of nucleotide probes employing concentrations of acridinium ester reagents in the low micromolar range and purification using normal gel filtration techniques. Such micromolar concentration ranges are only useful to label nucleotide probes to a low extent (less than or equal to 10%). Likewise, prior art separation techniques, including gel filtration, are not feasible as applied to acridinium ester labelled probe. We found that aggregated free acridinium ester label coeluted in the void volume with acridinium ester labelled probe. In addition, free acridinium ester label non-covalently associated with the probe and co-migrated with the acridinium ester labelled probe in the column. Finally, procedures known in the art were unsatisfactory for separating acridinium ester labelled probe from unlabelled probe.

Accordingly, objects of this invention include methods for labelling, with high efficiency, nucleic acid probes with acridinium ester. Another objective of this invention is methods for separating, to a high degree of purity, said labelled probe from unreacted as well as aggregated and non-covalently associated acridinium ester. Yet another objective of this invention is methods for separating said labelled probe from unlabelled probe and breakdown products of labelled probe. Yet another object of this invention is methods that are efficient, rapid, reproducible and able to produce large quantities of acridinium ester labelled oligomer of high purity, thereby making said labelled probe useful for diagnostic assays.

SUMMARY OF THE INVENTION

The acridinium ester 4-(2-succinimidyloxycarbonylethyl)phenyl-10-methylacridinium-9-carboxylate fluorosulfonate is a highly chemiluminescent compound which contains an amine reactive succinimidyl group. Reaction of this compound and similar compounds with rucleic acid probes containing primary amines yields a chemiluminescent labelled probe. In a related reaction system, nucleic acid probes containing thiols, and other amine and thiol conjugation partners also may be reacted with acridinium esters to yield a chemiluminescent labelled probe. This invention describes methods for the construction, labelling and subsequent purification of probe containing primary amines with acridinium ester, yielding a probe with a single acridinium ester per primary amine. Also described are related systems for the construction, labelling and subsequent purification of probe containing thiol groups with acridinium ester.

Probes are difficult to label using N-hydroxysuccinimidyl active ester labelling reagent concentrations in the low micromolecular range. Acridinium ester labelling of nucleotide probes is further complicated by the fact that acridinium esters are particularly unstable once attached to probes. This invention discloses a novel method for attaching acridinium esters to amine or sulfhydryl groups which comprise probes. These moieties, particularly amines are difficult to label with acridinium ester because they interact with the negatively charged phosphates of the probe.

The inventive method for attaching acridinium ester to probes involves use of high (0.1 to 50 mM) acridinium ester concentrations. These high concentrations may be achieved by using organic solvent in concentration of 20% to 80% by total reaction volume. Elevated pH also may be employed to increase the effective concentration of either the nucleophillic amino or thiol conjugation partners. The preferred method for labelling probe is to use 1–10 mM concentrations of acridinium ester with organic solvent. Such labelling methods may be carried out either in solution, or with one or the other of the acridinium ester or the probe suspended in solution.

Thus constructed, labelled probes may be purified using the inventive methods disclosed herein. Purification, or the separation of acridinium ester labelled probe from unlabelled probe as well as from free acridinium ester, involves first removing most of the free acridinium ester label from probe then removing substantially all remaining free label from the probe and finally, separating labelled probe, unlabelled probe and labelled probe decomposition products. These steps may be done sequentially or simultaneously.

Preferred methods for removing the majority of free label from probe are rapid separation techniques, including, without limitation, nucleic acid precipitation, ion exchange HPLC, and reverse phase HPLC. Preferred, methods for removing the remaining traces of free acridinium ester from probe and for simultaneously separating labelled probe from unlabelled probe involve specific applications of ion exchange, reverse phase or hydroxyapatite HPLC.

In this manner, nucleic acid probes may be labelled with acridinium ester and purified to a high degree of purity. Such labelled and purified probes may then be used in the field of diagnostic assays to detect minute amounts of specific target substances. Also included in this invention is a description of reagent and assay systems and kits used for detection of acridinium ester labelled probes.

BRIEF DESCRIPTION OF THE DRAWINGS

FIG. 3 is a chart summarizing conjugation partners and reaction products and conditions for labelling probe with acridinium ester.

DETAILED DESCRIPTION OF THE PREFERRED EMBODIMENTS DEFINITIONS

Figure 1:
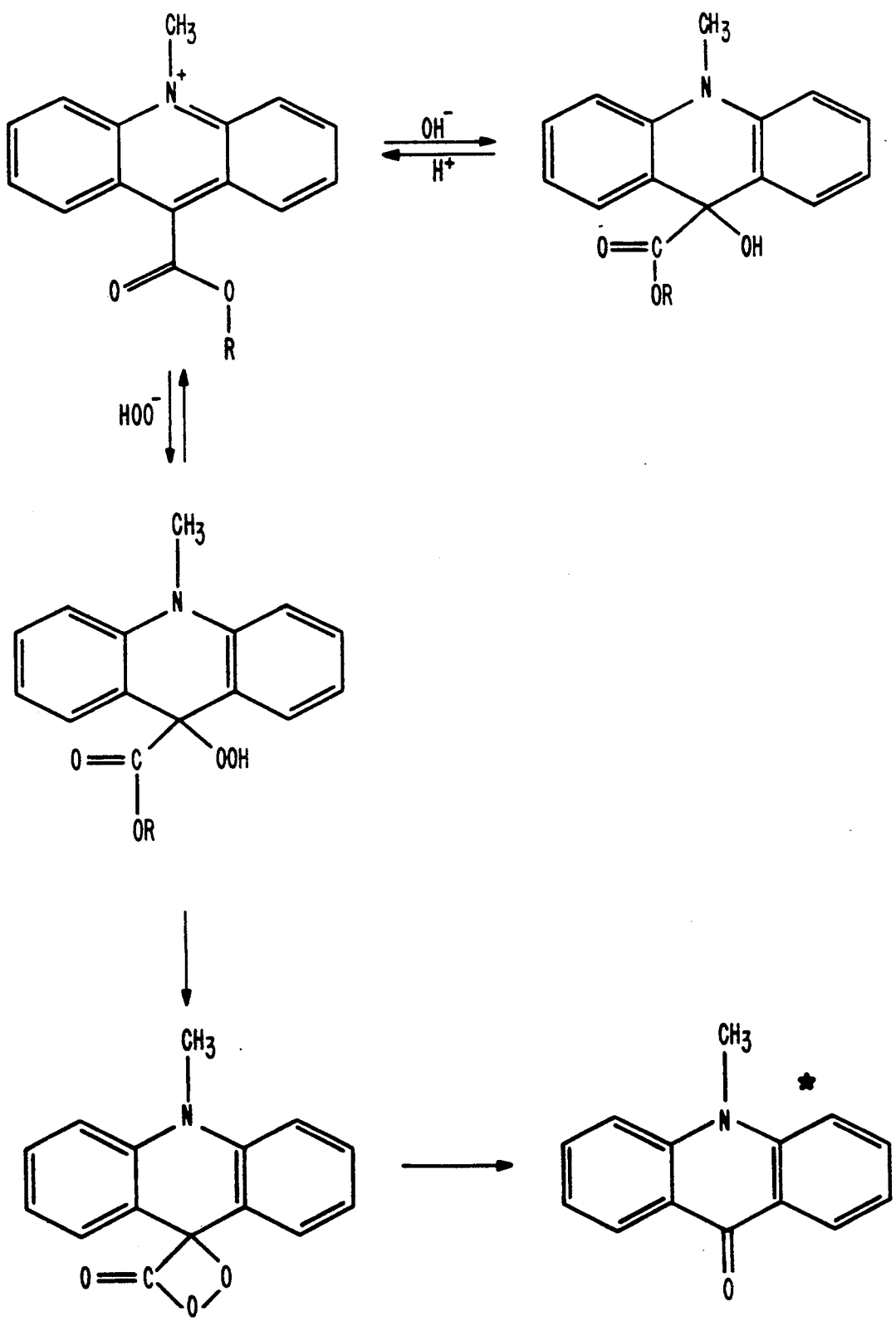
FIG. 1 is a graphical representation of the acridinium ester reaction scheme.

As used in this disclosure and claims, the following terms are defined as:

N-Hydroxysuccinimidyl ester of acridinium ester: derivative of acridine possessing a quaternary nitrogen center and derivatized at the 9 position to yield a phenyl ester moiety, specifically, 4-(2-succinimidyloxycarbonyl ethyl) phenyl-10-methylacridinium 9-carboxylate fluorosulfonate:

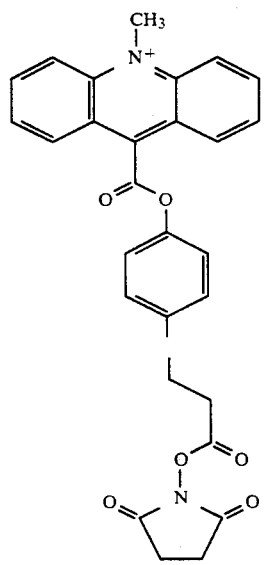

acridimium ester methoxyimidate:

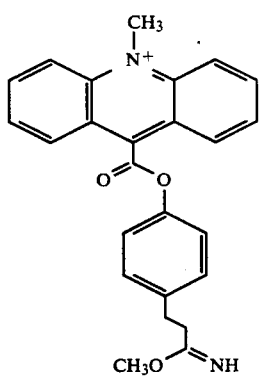

acridinium esters: moieties of the following general type

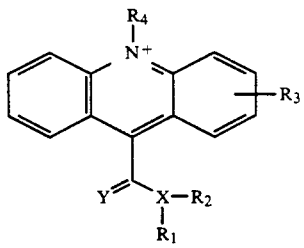

$R_1$ = ALKYL, ALKENYL, ARYL, SUBSTITUTED ALKYL, SUBSTITUTED ALKENYL, SUBSTITUTED ARYL, ALKOXY, ARYLOXY, OR IS ABSENT WHEN X=HALOGEN.

$R_2$ = H, ALKYL, ALKENYL, ARYL, SUBSTITUTED ALKYL, SUBSTITUTED ALKENYL, SUBSTITUTED ARYL, ALKOXY, ARYLOXY, IF ANY ONLY IF X=N.

$R_3$ = H, AMINO, HYDROXY, THIOL, HALOGEN, NITRO, AMINO, AMIDO, ACETYL, ALKYL, ALKENYL, ARYL, SUBSTITUTED ACETYL, SUBSTITUTED ALKYL, SUBSTITUTED ALKENYL, SUBSTITUTED ARYL, ALKOXY, ARYLOXY.

$R_4$ = ALKYL, ALKENYL, ARYL, SUBSTITUTED ALKYL, SUBSTITUTED ALKENYL, SUBSTITUTED ARYL.

X = O, N, S, HALOGEN, SUBSTITUTED PHOSPHOROUS, SUBSTITUTED SULFUR, SUBSTITUTED BORON, OR SUBSTITUTED ARSENIC.

Y = O, S, OR NH.

$R_1$ AND/OR $R_2$ AND/OR $R_3$ AND/OR $R_4$ HAS A REACTIVE SITE WHICH ALLOWS CHEMICAL CONJUGATION.

nucleotide: A subunit of a nucleic acid consisting of a phosphate group, a 5 carbon sugar and a nitrogen containing base. In RNA, the 5 carbon sugar is ribose. In DNA, it is a 2-deoxyribose. The term also includes analogs of such subunits.

nucleotide multimer: A chain of nucleotides linked by phosphodiester bonds, or analogs thereof.

oligonucleotide: A nucleotide multimer generally about 10 to about 100 nyucleotides in length, but which may be greater than 100 nucleotides in length. They are usually considered to be synthesized from nucleotide monomers, but may also be obtained by enzymatic means.

deoxyriboligonucleotide: An oligonucleotide consisting of deoxyribonucleotide monomers.

polynucleotide: A nucleotide multimer generally about 100 nucleotides or more in length. These are usually of biological origin or are obtained by enzymatic means.

nucleotide multimer probe: A nucleotide multimer having a nucleotide sequence complementary with a target nucleotide sequence contained within a second nucleotide multimer, usually a polynucleotide. Usually, the probe is selected to be perfectly complementary to the corresponding base in the target sequence. However, in some cases, it may be adequate or even desirable that one or more nucleotides in the probe not be complementary to the corresponding base in the target sequence. Typically, the probe is labelled. The shorthand reference "probe" shall be used throughout to refer to a nucleotide multimer probe as defined herein.

nucleotide/non-nucleotide polymer: A polymer comprised of nucleotide and non-nucleotide monomeric units. When used as a probe, it would typically be labelled.

hybrid: The complex formed between two nucleotide multimers by Watson-Crick base pairings between the complementary bases.

suspension: A mixture of liquids or a mixture of non-settling particles of a solid within a liquid, the particles liquid, the particles being the dispersed phase and the suspending medium being the continuous phase.

Acridinium ester chemistry generally has been described in Weeks et al. *Acridinium Esters as High-Specific Activity Labels in Immunoassay*, Clin. Chem. 2918, 1474–1479 (1983). Summarizing briefly, acridinium esters exist in equilibrium with their corresponding bases. Base formation is favored at high pH. Formation of the quaternary nitrogen species is favored at low pH. The chemiluminescence reaction involves attack by hydroxyperoxide ions on the acridinium species, which results in the formation of electronically excited N-methylacridone. The reaction is diagramed in FIG. 1 of the drawing.

1. Labeling with The N-Hydroxysuccinimidyl-Ester of Acridinium ester.

a. Selection of Probe.

Figure 2:
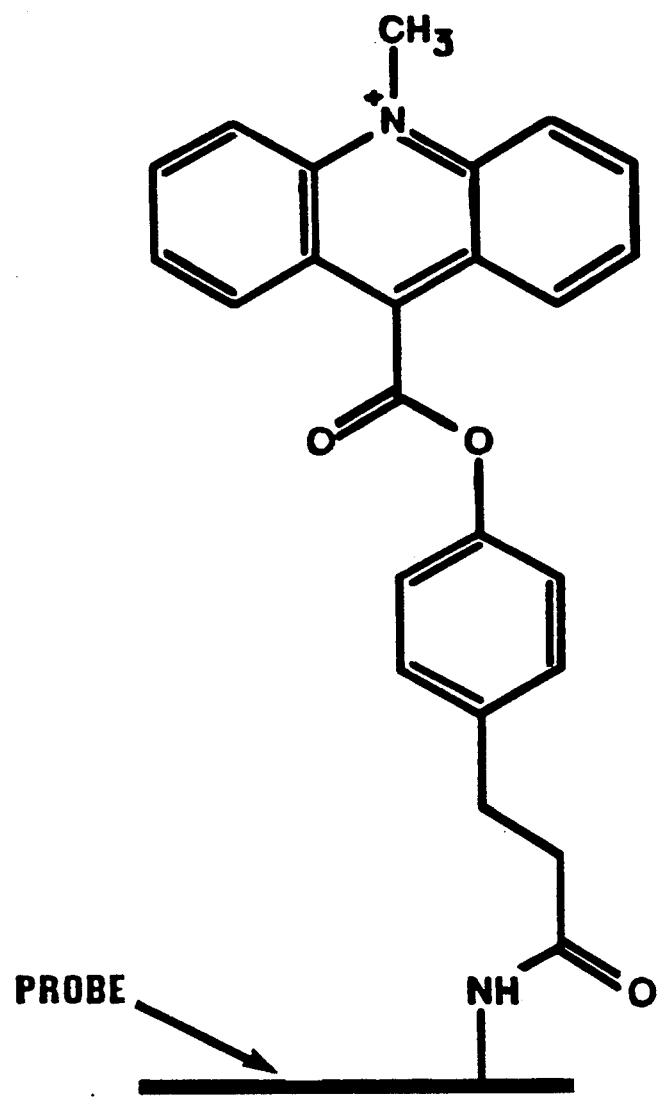
FIG. 2 is a graphical representation of a probe internally labelled with acridinium ester.

In the preferred embodiment, the probe to be labelled contains a primary amine. We have successfully practiced this method with amine linker-arm probes modified on the 5'-terminus (5'-aminoethyl phosphate; "terminal amine linker-arm"), modified internally (non-nucleotide based "internal amine linker-arm", types 1 (see L1 in patent application Ser. No. 099,050), 2 (see L3 in patent application Ser. No. 099,050), L2, L4, L5, L6, L7 or L8, used as either a base replacement or an insertion between bases) or adding amine-modified bases internally (amino (12)d UTP, Calbiochem, San Diego, CA), or on the 3'-end of the probe (5-allylamine UTP). In addition, the invention can be used to label, for example, the phosphate backbone and the sugar residues. The present invention contemplates the use of other modified rucleotide probes known in the prior art and mentioned in the prior-art section hereof, including, without limitation, amine linker arm probes, thiol phosphate containing probes and thiol uridine containing probes. FIG. 2 of the Drawing depicts a probe internally labelled with acridinium ester.

b. Labeling of Probe.

1. Selection of pH: This depends somewhat on the amine linker-arm, but the optimum pH is about 8 for this chemistry.

2. Selection of Buffer: Must be a good buffer at optimum pH. Possible choices include but are not limited to HEPES, phosphate, bicarbonate.

3. Selection of Organic Solvent: To be used in the range of 20% to 80% in final reaction cocktail. Choices include but are not limited to DMSO, $CH_2CN$, dimethyl formamide, dioxane, acetone methanol. The requirement for selection is that probe and the acridinium ester must be highly soluble in the selected solvent, and that the acridinium ester and probe not be unduly degraded by the solvent.

4. Acridinium Ester Concentration: Ranges between 0.1 mM to 50 mM are acceptable depending on the chemistry selected. The optimal range for the N-hydroxysuccinyimidyl ester conjugation partner is approximately 1–10 mM acridinium ester, depending on the amine linker-arm chemistry used. Multiple additions during the course of the reaction increase ultimate extent of labelling, but make purification more difficult.

5. Temperature: Optimal between 15°–40° C.

6. Duration of Reaction: This is dependent upon linkerarm chemistry and other reaction parameters and should be determined by analysis of time-point aliquots. One consideration in the analysis is the extent of labelling versus appearance of acridinium ester-probe breakdown products.

7. Quenching of Unreacted Electrophillic Conjugation Partners of N-hydroxysuccinimidyl-acridinium ester: Simple analogs of the conjugation partner nucleophile should be added under the same reaction conditions.

FIG. 3 summarizes reaction products and conditions of the invention for nucleic acid probes containing amines, thiols and their respective conjugation partners.

c. Purification of Labeled Probe.

A two-step procedure is typically more efficient. First, the majority of the free label should be removed using a fast and simple procedure. Examples of this include but are not limited to precipitation; binding of free label to hydroxyapatite, Bio-Beads SM-2, Sep-pak, or other solid support to which free label binds and labelled probe does not or vice versa; rapid gel filtration; extraction of free label into an organic phase; filtration (such as Centricon); rapid ion-exchange chromatography (including HPLC), or rapid reverse phase chromatography (including HPLC). Next, the labelled probe must be separated from any remaining free label, including acridinium ester which is non-covalently associated with the probe, to a very high degree of purity, and from unlabelled probe. The choices here are much more limited. The fastest and most efficient procedure is HPLC, including, but not limited to, ion-exchange, reverse phase, and hydroxyapatite. Another procedure we have found to work adequately, although not as well as HPLC and which is more tedious and time-consuming, is gel filtration in the presence of organic solvent, typically using Biogel P-100 or P-200 in formamide.

Purification can also be achieved in one step using HPLC, and using gel filtration in organic solvent if the quantities to be purified are small enough. This one-step procedure is typically not as efficient as the two-step procedure described above.

WORKING EXAMPLES

EXAMPLE 1

Labeling and Purification via Ethanol Precipitation followed by Ion-exchange HPLC of a Variety of Amine Linker-Arm Probes.

A. Synthesis and Purification of Amine Linker-Arm Probes.

In order to demonstrate the successful application of the methods and procedures described herein to a variety of deoxyoligonucleotide probes with a variety of amine linker-arm chemistries, the following amine linker-arm probes were prepared.

1.5'-amine linker-arm probes

To attach a 5'-amine linker-arm to probe, two approaches were used. One was to use the commercially available reagent "Aminolink" from Applied Biosystems, Inc. The other was to use the following compound:

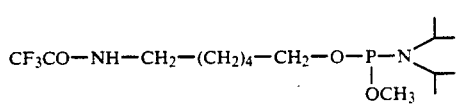 (1)

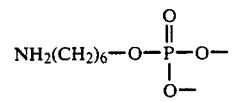

This compound will heretofore be referred to as terminal amine linker-arm reagent. This reagent was synthesized as follows: 6-amino hexanol was reacted with S-ethyltrifluorothioacetate in anhydrous ethylacetate. The reaction product was precipitated in petroleum ether, treated with a 10% pyridine in water mixture for 10 minutes to hydrolyze any O-trifluoroacetyl which may have formed, and evaporated to dryness in the form of a gum. This compound was then phosphitylated according to standard protocols within the literature (see Nucleic Acids Research, 12 (11), 4539 (1984)) to yield the desired compound, namely, terminal amine linker-arm reagent (1).

Probes containing a 5'-amine linker-arm (either Aminolink or terminal amine linker-arm) were synthesized as follows. Using an Applied Biosystems, Inc. Model 380A DNA synthesizer, probes of desired nucleotide sequence were produced using standard phosphoramidite chemistry, building the probes from the 3'-end to the 5'-end. After the desired sequence was completed, amine linker-arm was automatically coupled to the 5'-hydroxyl group of the probe using either terminal amine linker-arm reagent in the same way another phosphoramidite nucleoside would have been coupled, or Aminolink using the procedure described by the manufacturer. Using standard protocols, the probe was then cleaved from the solid support and deprotected using NH4OH and purified by polyacrylamide gel electrophoresis followed by Sephadex G-25 chromatography.

The following probes were synthesized and purified using this procedure:

where represents the amine linker-arm, and

where

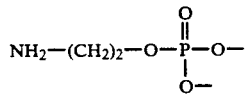

represents Aminolink.

2, Internal amino linker-arm probes.

To incorporate an amine linker-arm into the internal portion of a probe, internal amine linker-arm reagent, type 1 or type 2, was used as described in U.S. Pat. application Ser. No. 099,050 entitled "Non-Nucleotide Linking Reagents for Nucleotide Probes" filed Sep. 21, 1987, by Arnold, et al. Again, probes were synthesized using standard phosphoramidite chemistry and purified using polyacrylamide gel electrophoresis and Sephadex G25 chromatography.

The following probes were synthesized using this procedure:

1.) A 30 mer complementary to the 16S subunit of rRNA from *E. coli*, with an internal amine linker-arm, type 1, replacing an adenine residue at position 18 in the sequence:

```
                    Replaced with an internal amine linker arm, type 1
                                         |
5'-CCA CTG CTG CCT CCC GT (A) GGA GTC TGG GCC-3'
```

Probes also were synthesized in this manner where internal linker-arm, type 1, replaced thymidine, cytidine or guanosine residues.

2.) A 33 mer complementary to the 16S subunit of rRNA from *Chlamydia trachomatis*, with an internal amine linker-arm, type 1, replacing an adenine residue at position 21 in the sequence.

```
                        Replaced with an internal amine linker arm, type 1
                                             |
5'-CGT TAC TCG GAT GCC CAA AT (A) TCG CCA CAT TCG-3',
or inserted between residues 21 and 22, An internal amine linker-arm, type 1 or type 2,
                              inserted here
                                           ▼
5'-CGT TAC TCG GAT GCG CAA ATA TCG CCA CAT TCG-3'
```

3.) A 24 mer complementary to the 23S subunit of rRNA from *Chlamydia trachomatis*, with an internal linker-arm, type L7, inserted between residues 15 and 16,

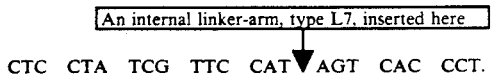

CTC CTA TCG TTC CAT▼AGT CAC CCT.

B. Labeling of Amine Linker-Arm Probes with the NHS ester of Acridinium Ester and Subsequent Purification.

A 25 mM stock solution of the NHS ester or acridinium ester was prepared in distilled DMSO. The desired amount of probe (see a listing of the different probes labelled in section A above) was evaporated to dryness in a 1.5 ml conical polypropylene tube. The following cocktail was constructed by adding the following ingredients in the order listed:
  3 microliters $H_2O$
  1 microliter 1M HEPES (pH 8.0)
  4 microliter DMSO (distilled)
  2 microliters 25 mM NHS ester of acridinium ester in DMSO (distilled)

The mixture was vortexed, spun in a microcentrifuge for 2 seconds (to bring the contents to the bottom of the tube), and incubated at 37° C. for 20 minutes. The following components were then added to the reaction cocktail in the order listed:
  3.0 microliters 25 mM NHS ester of acridinium ester in DMSO (distilled)
  1.5 microliters $H_2O$
  0.5 microliter 1M HEPES (pH 8.0)

The cocktail again was vortexed, spun, and incubated an additional 20 minutes at 37° C. The unreacted label was quenched using a 5-fold excess of lysine by adding 5 microliters of 0.125M lysine in 0.1M HEPES (pH 8.0), 50% DMSO, and incubated 5 minutes at room temperature.

The acridinium ester-labelled probe was then purified using the following methods. In order to remove the majority of the unreacted label, the probe was ethanol precipitated as follows: to the 20 microliters quenched reaction mixture 30 microliters 3M NaOAc (pH 5.0), 245 microliters $H_2O$ and 5 microliters glycogen was added as a carrier (the glycogen was pre-treated to remove any nuclease activity). The sample was vortexed briefly and 640 microliters of absolute EtOH added. The sample was vortexed briefly and incubated on ice 5–10 minutes, then centrifuged 5 minutes at 15,000 rpm in a microcentrifuge. The supernatant was carefully removed and the pellet was redissolved in 20 microliters of 0.1M NaOAc (pH 5.0), 0.1% SDS. The AE-labelled probe was then separated from any remaining free label, from unlabelled probe and from breakdown products of AE-labelled probe by one of two HPLC systems described below:

ION-EXCHANGE HPLC

Figure 4A:
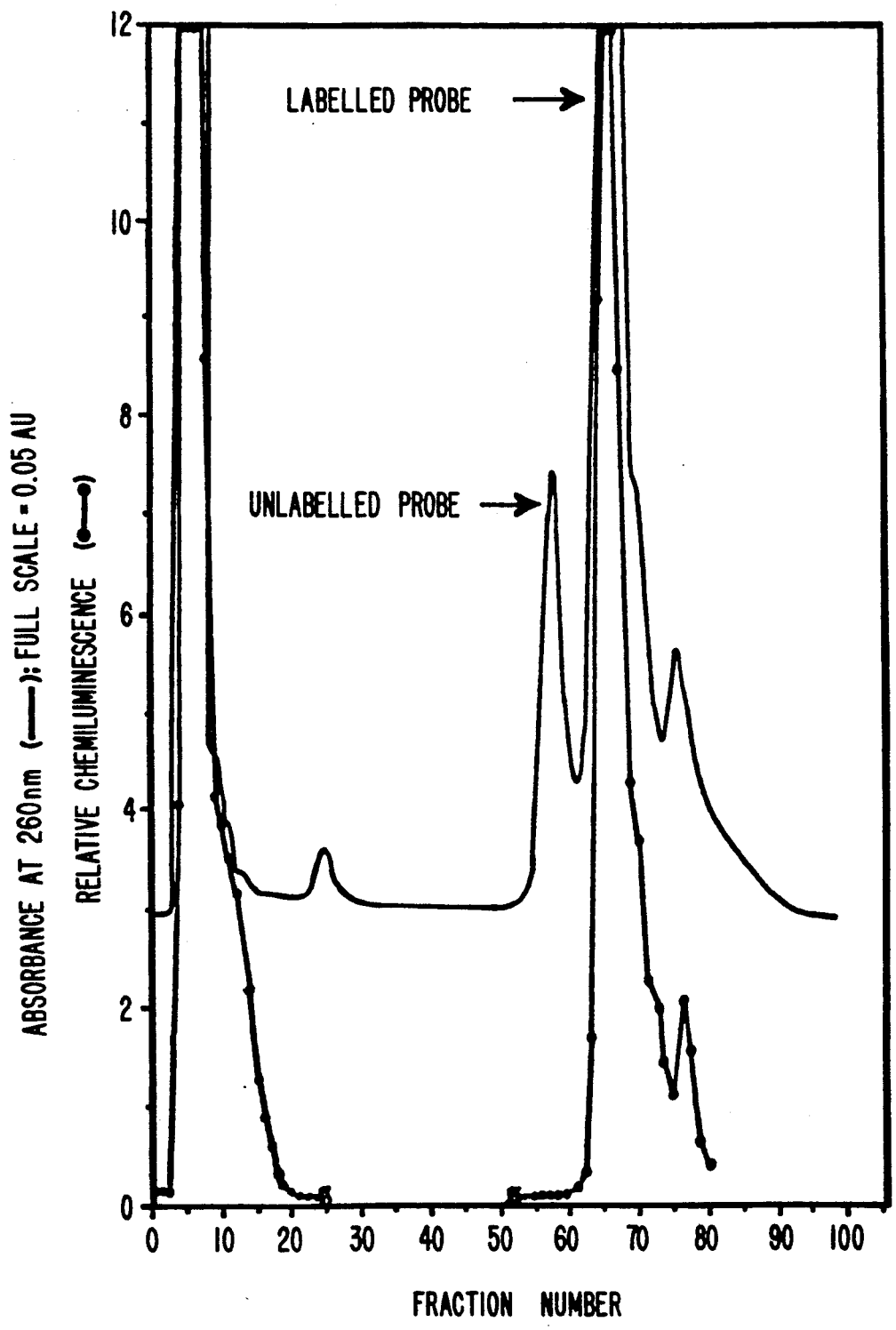
FIG. 4 is a graphical representation of an ion exchange (4A) and a reverse phase (4B) HPLC profile of an acridinium ester labelled probe.

The 20 microliters redissolved pellet was injected onto a Nucleogen-DEAE 60-7 ion-exchange HPLC column mounted in an IBM 9533 HPLC system. All buffers were made with HPLC grade water, acetonitrile ($CH_3CN$) and sodium acetate (NaOAc) from Fisher Scientific, and reagent grade glacial acetic acid (HOAC) and LiCl. All buffers were filtered through 0.45 micromole pore size Nylon-66 filters before use. Elution was achieved with a linear gradient from 55% of Buffer A, 45% Buffer B to 30% Buffer A, 70% Buffer B in 25 minutes at a flow rate of 0.5 ml/min. Absorbance at 260 mn was monitored during the run; field range equal 1 O.D. unit; chart speed was 20 cm/hr. Fractions of 0.5 ml were collected in 1.5 ml screw-capped Eppendorf tubes. The results are depicted in FIG. 4A (in this case the probe was the terminate, amine linker-arm containing 26 mer described in Section A above; all other probes gave very similar profiles). Immediately after the run, 5 microliters of 10% SDS was added to each tube followed by vortexing of each tube (this was done to ensure that the acridinium ester-labelled probe did not stick to the walls of the tube). A 0.5 microliter aliquot was removed from fractions 21–42 and added to 200 microliters water in a 12×75 mm tube (a separate pipet tip was used for each aliquot to avoid a carryover problem). The chemiluminescence of each aliquot was then determined in a Berthold Clinilumat using the following automatic injection and read sequence: injection of 200 microliters of 0.25N $HNO_3$, 0.1% $H_2O_2$; a 1 second delay; a 200 microliter injection of 1N NaOH; read chemiluminescent output for 10 seconds.

Fractions 64–68 were then EtOH precipitated as follows: Add to each 5 microliters glycogen, vortex, add 1 ml EtOH, vortex, incubate 5–10 minutes on ice, and centrifuge 5 minutes at 15,000 rpm in a microcentrifuge. Each supernatant was carefully removed, the pellet redissolved in 20 microliters 0.1M NaOAc, pH 5, 0.1% SDS, and the fractions were pooled.

REVERSE PHASE HPLC

Figure 4B:
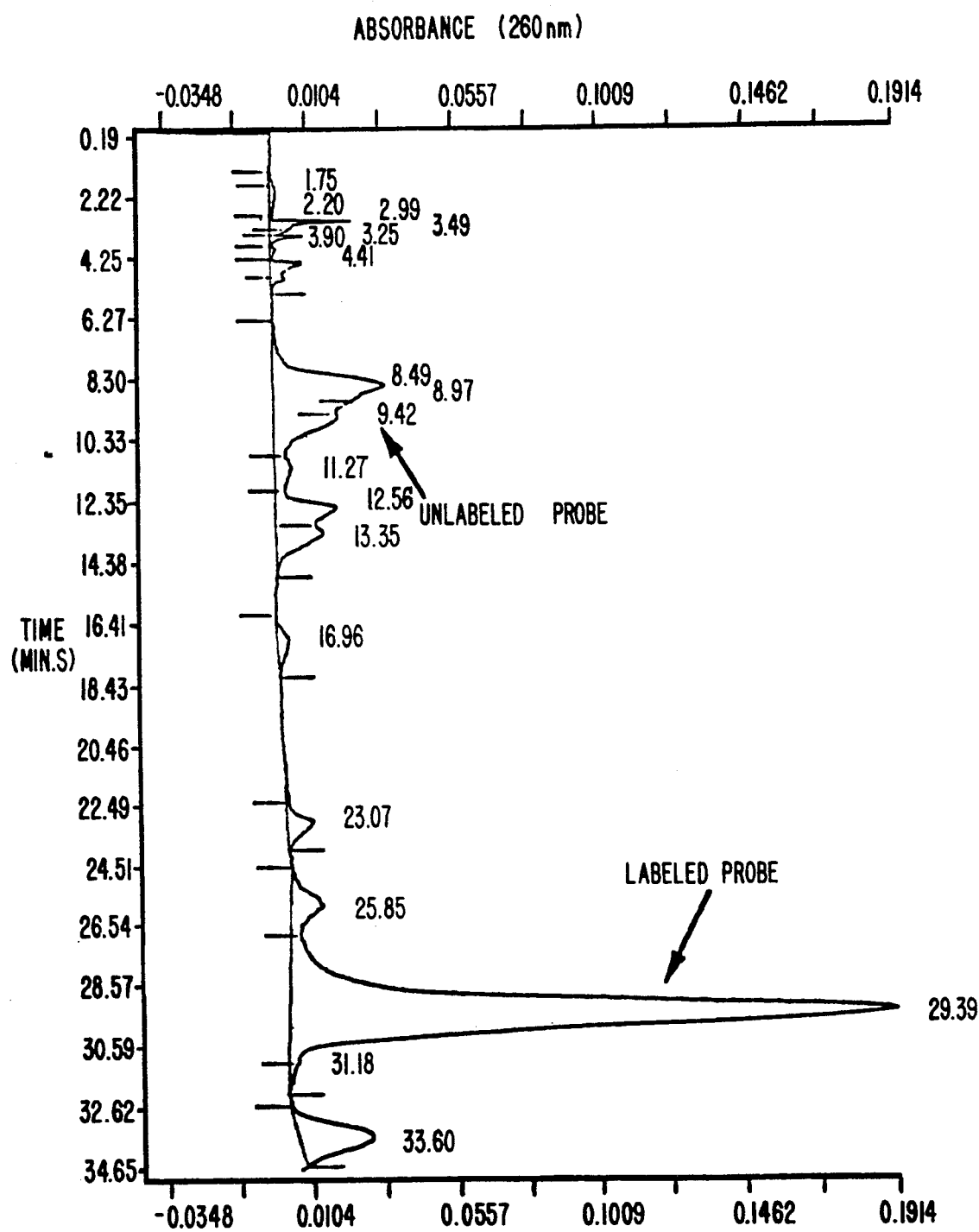

Acridinium ester-labelled probe was also purified generally as described above, with the following exceptions: A Vydac C4 reverse phase column was used; buffer A was 0.1M triethylammonium acetate (Applied Biosystems, Inc., Foster City, CA) and buffer B was $CH_3CN$; the labelled probe was eluted using a linear gradient from 10–15% solvent B in 25 minutes at a flow rate of 1 ml/min; absorbance was monitored at 260 nm; 0.5 ml fractions were collected. The main chemiluminescent peak was then identified and worked up as described above (except that 45 microliters of 3M NaOAc was also added to each fraction before EtOH precipitation). FIG. 4B of the drawing shows the elution profile of the 24 mer probe (internal linker-arm, type L7) described in Section A above; all other probes gave very similar profiles.

Figure 5:
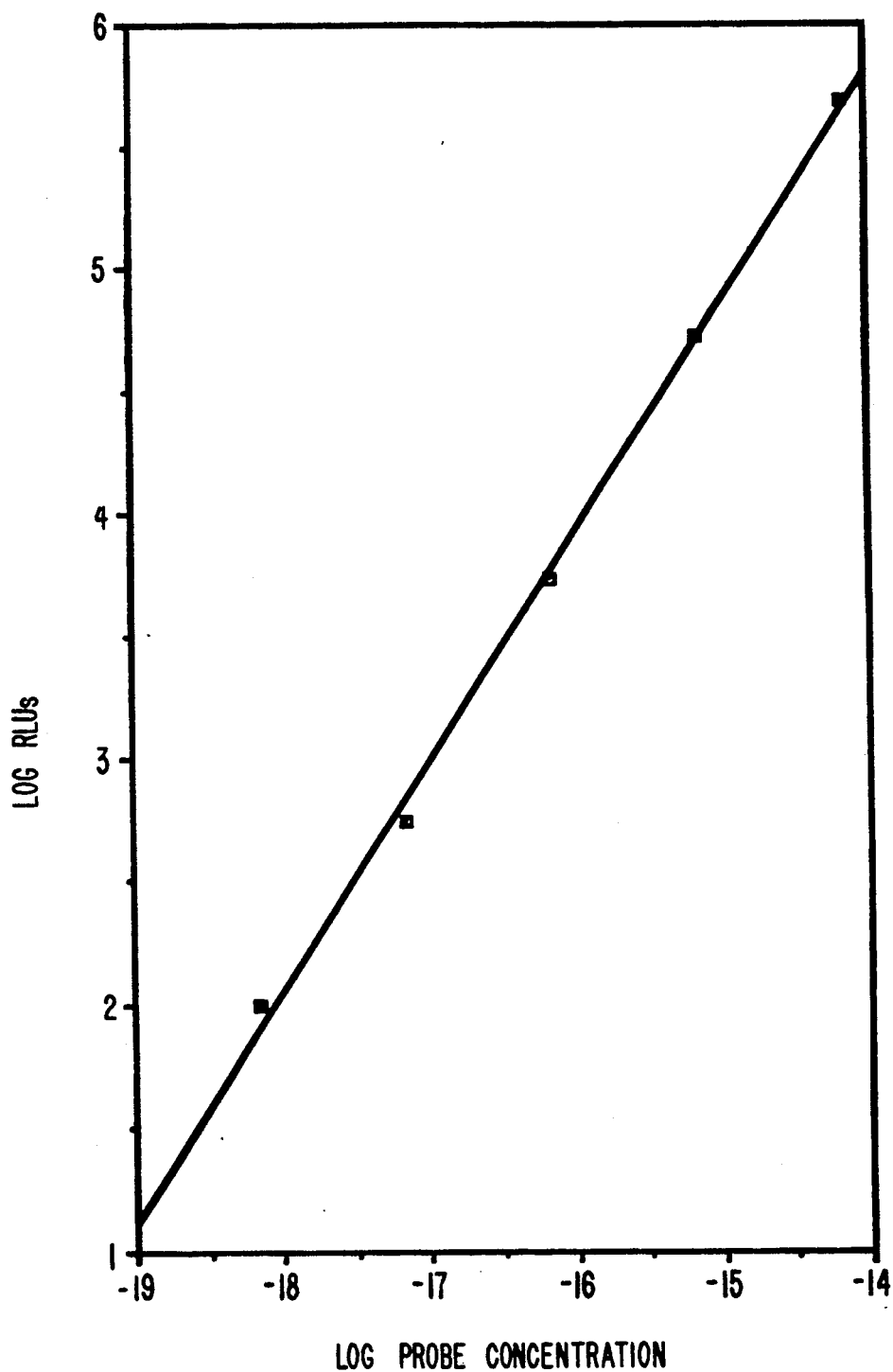
FIG. 5 is a graphical representation of detection of acridinium ester labelled probes.

Using both of these procedures, highly pure acridinium ester-labelled probes were obtained with essentially equivalent results with all linker-arm chemistries referred to herein. The specific activity of such probes was typically 5–10×10' chemiluminescent light counts (Berthold Clinilumat) per picomole of probe. FIG. 5 of the drawing shows the sensitivity with which such probes can be detected once purified.

C. Labeling of Amine-Linker-Arm Probe with the Methoxyimidate Derivative of Acridinium Ester and Subsequent Purification.

The procedure was generally the same as that described in Section B, with the following differences: The dried probe was redissolved in 50 microliters 0.5M $NaCO_3$, pH 9, plus 25 microliters dimethylformamide. Next, 0.2 mg of methoxyimine acridinium ester (MI-AE) was added, the mixture was vortexed and allowed to react 30 minutes at room temperature. An additional 0.2 mg of MI-AE was added, and reaction continued an additional 30 minutes at room temperature. The unreacted label was quenched with 100 microliters of 50 mM lysine in 0.5M NaHCO$_3$, pH 9 (10 minute incubation at room temperature).

The acridinium ester-labelled probe was then ethanol precipitated as described in Section A, except 40 microliters of 3M NaOAc (pH 5.0), 105 microliters of H$_2$O, and 750 microliters of absolute EtOH were used. The probe then was further purified using ion-exchange HPLC as described in Section B.

EXAMPLE 2

Detection of a Dilution Series of Target Polynucleotide Sequence in Clinical Media Using an Acridinium Ester Labelled Probe.

Probe labelled internally with acridinium ester (33 mer, internal linker-arm, type 1, adenosine replacement; see Example 1) was hybridized to its target rRNA (in this case *Chlamydia trachomatis*) according to the following procedure:

Hybridization Mixture 16 microliters throat swab in 3% lithium lauryl sulfate, 30 mM phosphate buffer (PB) pH 6.8, 1 mM EDTA, 1 mM EGTA.

2 microliters 4.8M PB, pH 4.7

1 microliter rRNA ($10^{-3}$, $10^{-2}$, $10^{-1}$, or 0.33 micrograms)

1 microliter probe (0.33 pmol)

The control mixture was the same as the hybridization mixture except that it contained water instead of rRNA. The mixtures were incubated 60 minutes at 60 degrees Celsius. Hybrid was then separated from nonhybridized probe using hydroxyapatite (HAP) as follows: To each hybrid and control mixture was added 150 microliters of 0.14M PB, pH 6.8, containing 2% HAP. Each resulting mixture was vortexed 5 seconds, incubated 5 minutes at 60 degrees Celsius, vortexed 20 seconds, then centrifuged 30 seconds in a microcentrifuge at 15,000 rpm. The supernatant was removed, 150 microliters of 0.14M PB, pH 6.8, was added to the HAP pellet, the mixture was vortexed 10 seconds, then centrifuged 30 seconds in a microcentrifuge at 15,000 rpm. The supernatant was removed, and this washing procedure was repeated two more times in exactly the same fashion. The remaining HAP pellet was resuspended in 150 microliters of 0.14M PB, pH 6.8, and read directly for chemiluminescence exactly as described in Example 1.

|  | Signal | S:B |
| --- | --- | --- |
| Control (no rRNA) | 18 | — |
| $10^{-3}$ micrograms rRNA | 27 | 1.5 |
| $10^{-2}$ micrograms rRNA | 117 | 6.5 |
| $10^{-1}$ micrograms rRNA | 933 | 52 |
| 0.33 micrograms rRNA | 2756 | 153 |

Results represent the average of duplicate values. Signals given as thousands of relative light units (rlu's). Control signal represents approximately 0.1% of input rlu. S:B is the signal to background ratio, i.e., chemiluminescence at a particular rRNA concentration divided by chemiluminescence of control.

These data demonstrate that probes labelled with acridinium ester and purified as described herein can subsequently be used to sensitively and specifically detect target polynucleotide sequences.

We claim:

1. A method for labelling a nucleic acid probe having a first conjugation moiety, with an acridinium ester labelling reagent having a second conjugation moiety, including the step of:

combining said labelling reagent and said nucleic acid probe so as to effectuate a labelling reagent concentration of approximately 0.1–50 mM to obtain acridinium ester labelled nucleic acid probes in high yield.

2. A method as in claim 1 wherein the step is carried out in the pH range 7–9.

3. A method as in claim 2 wherein the step is carried out in the temperature range 15–40 degrees Celsius.

4. A method as in claim 1 or 2 or 3 wherein the step is carried out in solution.

5. A method as in claim 1 or 2 or 3 wherein the step is carried out with said nucleic acid probe in solution and wherein said labelling reagent is suspended in solution.

6. A method as in claim 1 or 2 or 3 wherein the step is carried out with said labelling reagent in solution and said nucleic acid probe is suspended in solution.

7. A method for labelling a nucleic acid probe having a first conjugation moiety, with an acridinium ester labelling reagent having a second conjugation moiety, including the step of:

combining said labelling reagent and said nucleic acid probe in a manner so as to effectuate a labelling reagent concentration of approximately 0.1–50 mM and an organic solvent concentration of approximately 20% to 80% by volume to obtain acridinium ester labelled nucleic acid probes in high yield.

8. A method as in claim 7 wherein the step is carried out in pH range 7–9.

9. A method as in claim 7 wherein the step is carried out in the temperature range 15–40 degrees Celsius.

10. A method as in claim 7 or 8 or 9 wherein the step is carried out in solution.

11. A method as in claim 7 or 8 or 9 wherein the step is carried out with said nucleic acid probe in solution and wherein said labelling reagent is suspended in solution.

12. A method as in claim 7 or 8 or 9 wherein the step is carried out with said labelling reagent in solution and said nucleic acid probe is suspended in solution.

13. The method of claim 7 wherein said organic solvent is selected from the group consisting of DMSO, CH$_3$CN, dimethyl formamide, dioxane, acetone and methanol.

14. A method for labelling nucleic acid probes having a first conjugation moiety with an acridinium ester labelling reagent having a second conjugation moiety, including the steps of:

combining said labelling reagent in approximately a 0.1–50 mM concentration;

with an organic solvent in concentration of approximately 20% to 80% by volume to obtain acridinium ester labelled nucleic acid probes in high yield;

quenching the unreacted labelling reagent.

15. A method for labelling nucleic acid probes having a first conjugation moiety with an acridinium ester labelling reagent having a second conjugation moiety, including the steps of:

combining said labelling reagent in approximately a 0.1–50 mM concentration with an organic solvent in a 20% to 80% concentration by volume to obtain acridinium ester labelled nucleic acid probes in high yield, wherein said first and second conjugation moieties are selected, respectively from the group of pairs consisting of:

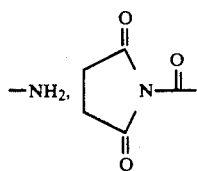 in pH range 7-9; (1)

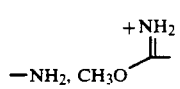 in pH range 8-10; (2)

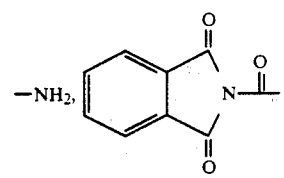 in pH range 7-9; (3)

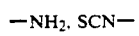 in pH range 7-9; (4)

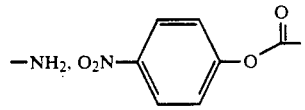 in pH range 7-9; (5)

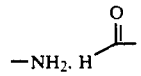 in pH range 7-9; (6)

-continued

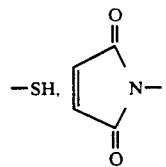 in pH range 6-8; (7)

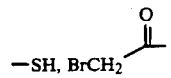 in pH range 6-8; (8)

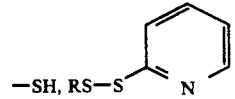 in pH range 6-9; (9)

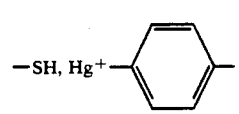 in pH range 5-9. (10)

with an organic solvent in concentration of approximately 20% to 80% by to volume in acridinium ester labelled nucleic acid probes in high yield.

16. A method for labelling nucleic acid probes having a first conjugation moiety with an N-hydroxysuccinimide-acridinium ester labelling reagent, comprising the step of combining said labelling reagent in approximately a 1-10 mM concentration with an organic solvent in concentation of approximately 20% to 80% by volume, to obtain acridinium ester labelled nucleic acid probes in high yield.

17. A method for labelling nucleic acid probes having a first conjugation moiety with an acridinium ester-methoxyimidate labelling reagent, comprising the step of combining said labelling reaGent in approximately a 1-10 mM concentration with an organic solvent in concentration of approximately 20% to 80% by volume, to obtain acridinium ester labelled nucleic acid probes in high yield.

* * * * *